United States Patent
Lin et al.

(10) Patent No.: US 8,337,818 B2
(45) Date of Patent: Dec. 25, 2012

(54) POST-FOAMING DENTAL MOUSSE AND METHODS UTILIZING THE SAME

(75) Inventors: Nora Lin, Basking Ridge, NJ (US); John Curtis, Greenbackvile, VA (US); James Brown, Edison, NJ (US)

(73) Assignee: Colgate-Palmolive Company, New York, NY (US)

( * ) Notice: Subject to any disclaimer, the term of this patent is extended or adjusted under 35 U.S.C. 154(b) by 718 days.

(21) Appl. No.: 11/260,116

(22) Filed: Oct. 27, 2005

(65) Prior Publication Data

US 2006/0093558 A1    May 4, 2006

Related U.S. Application Data

(60) Provisional application No. 60/624,608, filed on Nov. 3, 2004.

(51) Int. Cl.
*A61K 8/00* (2006.01)
*A61K 8/18* (2006.01)
*A61Q 11/00* (2006.01)

(52) U.S. Cl. .................................................. 424/49
(58) Field of Classification Search ............... 424/49
See application file for complete search history.

(56) References Cited

U.S. PATENT DOCUMENTS

| | | |
|---|---|---|
| 2,968,628 A | 1/1961 | Reed et al. |
| 3,541,581 A | 11/1970 | Monson et al. |
| 3,963,147 A | 6/1976 | Waters |
| 4,171,757 A | 10/1979 | Diamond |
| 5,057,309 A * | 10/1991 | Hill et al. .................. 424/52 |
| 5,071,637 A | 12/1991 | Pellico |
| 5,328,692 A | 7/1994 | Dana |
| 5,500,211 A | 3/1996 | George et al. |
| 5,560,859 A | 10/1996 | Hartmann et al. |
| 5,776,435 A | 7/1998 | Gaffar et al. |
| 6,010,683 A * | 1/2000 | Fischer ........................ 424/52 |
| 6,139,820 A | 10/2000 | Fischer et al. |
| 6,251,369 B1 * | 6/2001 | Stoltz ......................... 424/45 |
| 6,290,933 B1 | 9/2001 | Durga et al. |
| 6,602,491 B2 | 8/2003 | Hall et al. |
| 6,622,943 B2 | 9/2003 | Poisson et al. |

(Continued)

FOREIGN PATENT DOCUMENTS

AU    55530 80    7/1981

(Continued)

OTHER PUBLICATIONS

Taylor, A.J. et al., "Flavour Analysis Under Dynamic Conditions: Measuring the True Provile Sensed by Consumers", pp. 255-260.

(Continued)

*Primary Examiner* — Benjamin Packard
(74) *Attorney, Agent, or Firm* — Howard C. Lee

(57) ABSTRACT

A post foaming oral care mousse is provided by the invention. The mousse includes at least a dentifrice composition and a compressed liquid propellant having a boiling point less than −10° C. The liquid propellant is blended into the mousse as an emulsion, and the emulsion is adapted to be dispensed from a container as a gel that foams after a time delay. The mousse has a viscosity of less than 30,000 centipoise when measured prior to the addition of the propellant. Preferably, the mousse expands at least 100 vol % in less than 5 seconds upon exposure to atmospheric pressure.

22 Claims, 4 Drawing Sheets

U.S. PATENT DOCUMENTS

| | | | |
|---|---|---|---|
| 6,685,921 | B2 | 2/2004 | Lawlor |
| 6,789,702 | B2 | 9/2004 | O'Connor et al. |
| 2003/0206874 | A1 | 11/2003 | Doyle et al. |

FOREIGN PATENT DOCUMENTS

| | | |
|---|---|---|
| DE | 36 23 934 A1 | 1/1988 |
| DE | 100 08836 | 8/2001 |
| DE | 100 08839 | 9/2001 |
| EP | 0 208 009 A | 1/1987 |
| GB | 1317771 | 5/1973 |
| JP | S55-085513 A | 6/1980 |
| JP | S58-500740 | 11/1982 |
| JP | S62-042917 A | 2/1987 |
| JP | 03 07781 | 4/1991 |
| JP | 2003-073228 A | 3/2003 |
| JP | 2004-307357 A | 11/2004 |
| JP | 2006-500329 | 1/2006 |
| WO | WO 82/03975 | 11/1982 |
| WO | WO 01/62209 | 8/2001 |
| WO | WO 01/62210 | 8/2001 |
| WO | WO 0162211 A2 * | 8/2001 |

OTHER PUBLICATIONS

Brahms et al., 1996, "Investigation of the Interaction between Dentifrice Flavor and Product Base by Principal Component Analysis of Headspace-Gas Chromatography," Flavor-Food Interactions 633:73-86.

Cook et al., 2003, "Oral Shear Stress Predicts Flavour Perception in Viscous Solutions," Chem. Senses 28:11-23.

Cook et al., 2003, "Effects of Viscosity on Flavor Perception: A Multimodal Approach," *Challenges in Taste Chemistry and Biology*, American Chemical Society 867:240-253.

Cook et al., 2003, "Effects of Hydrocolloid Thickeners on the Perception of Savory Flavors," Journal of Agricultural and Food Chemistry.

Davidson et al., 1999, "Effect of Sucrose on the Perceived Flavor Intensity of Chewing Gum," J. Agric. Food Chem. 47:4336-4340.

Grab, 2000, "Flavorspace—a New Technology for the Measurement of Fast Dynamic Changes of the Flavour Release During Eating," Front. Flavour Sci. [Proc. Weurman Flavour Res. Symp.], 9th Meeting Date 1999, P.E. Schieberle, Karl-Heinz. Garching, Germany, Deutsche Forschungsanstalt fuer Lebensmittelchemie: 261-270.

Haahr et al., 2004, "Release of Peppermint Flavour Compounds from Chewing Gum: Effect of Oral Functions," Physiology and Behavor 82(2,3):531-540.

Halpern, 2004, "When Are Oral Cavity Odorants Available for Retronasal Olfaction?" *Handbook of Flavor Characterization*, F.S.A. Technology, New York, NY Marcel Dekker Inc. 131:51-63.

Harvey et al., 2000, "Real Time Flavour Release from Chewing Gum During Eating," Front. Flavour Sci. [Proc. Weurman Flavour Res. Symp.], 9th Meeting Date 1999, P.E. Schieberle, Karl-Heinz. Garching, Germany, Deutsche Forschungsanstalt fuer Lebensmittelchemie: 271-274.

Hodgson et al., 2003, "Simultaneous Real-Time Measurements of Mastication, Swallowing, Nasal Airflow, and Aroma Release," Journal of Agricultural and Food Chemistry 51:5052-5057.

Hollowood et al., 2002, "Taste Release and Its Eddect on Overall Flavor Perception," Chemistry of Taste, American Chemical Society 825:166-178.

International Search Report and Written Opinion in International Application No. PCT/US05/038947 mailed May 31, 2006.

Linforth, 2002, "Modelling Flavor Release," Food Flavour Technology, A.J. Taylor, Sheffield, UK, Sheffield Academic Press pp. 185-209.

Linforth et al., 2002, "Retronasal Transport of Aroma Compounds," Journal of Agricultural and Food Chemistry 50:1111-1117.

Linforth et al., 2004, "Novel Mass Spectrometric Techniques for Monitoring Aroma Volatiles," Handbook of Flavor Characterization F.S.A. Technology New York, NY Marcel Dekker Inc. 131:401-409.

Wright et al., 2003, "Persistence Effects in Flavour Release from Liquids in the Mouth," International Journal of Food Science and Technology 38(3):343-350.

Taylor, A.J. et al., "Atmospheric pressure chemical ionisation mass spectrometry for in vivo analysis of volatile flavour release", Food Chemistry, 2000, vol. 71, pp. 227-238.

Taylor, AJ et al, Flavour analysis under dynamic conditions measuring the true profile sensed by consumers. in: Frontiers of Flavour Science (2000) (eds Schieberie and Heinze), Deutsche Forschungsanstalt fur Lenensmittel, Garching, Germany, pp. 255-260.

* cited by examiner

POST-FOAMING DENTAL MOUSSE AND METHODS UTILIZING THE SAME

CROSS-REFERENCE TO RELATED APPLICATION

This application claims the benefit of priority to U.S. Provisional Application Ser. No. 60/624,608, filed Nov. 3, 2004, the contents of which are incorporated herein by reference.

BACKGROUND OF THE INVENTION

Numerous oral care compositions have been developed with the aim of providing therapeutic benefits to consumers, such as caries reduction and to treat, prevent or ameliorate various oral diseases and conditions. Improvements in the non-therapeutic aspects of oral care products, such as the development of improved textures, the inclusion of flavors and an improvement in the aesthetic appeal have been devised. Advantages of these formulations include increased compliance by consumers with tooth-cleaning regime, which may result in improved oral and overall health. In view of oral care consumers constantly evolving preferences for oral care products that deliver therapeutic as well as non-therapeutic aspects, there remains a need in the art for dentifrices of aesthetic and gustatory appeal that simultaneously provide therapeutic benefits to the consumer.

BRIEF SUMMARY OF THE INVENTION

The invention described herein relates to an oral care mousse that provides unique aesthetic, olfactory and gustatory benefits while also optionally providing the consumer with the therapeutic benefits similar to or better than conventional dentifrices. Specifically, the invention provides a post foaming oral care mousse. The mousse includes (a) a dentifrice composition that contains at least a surfactant and a humectant; and (b) a compressed liquid propellant that has a boiling point of less than about −10° C. The dentifrice composition has a viscosity of less than about 30,000 centipoise. After incorporation of the propellant, the mousse is dispensed as a gel that expands at least about 100 vol % in less than about 5 seconds. The mousse and/or dentifrice composition may contain various other ingredients, including therapeutic and/or cosmetic active ingredients.

The invention also include oral care mousses, as described above, and which upon application of the mousse to a user's oral cavity for 60 seconds has a flavor release peak ($P_m$) that is greater then the flavor release peak height of a control composition ($P_p$) containing the same flavorant or that exhibits an average rate of flavor release is 4000 units/sec to 20,000 units/sec in the initial 60 seconds after application to the oral cavity.

DETAILED DESCRIPTION OF THE INVENTION

Figure 1:
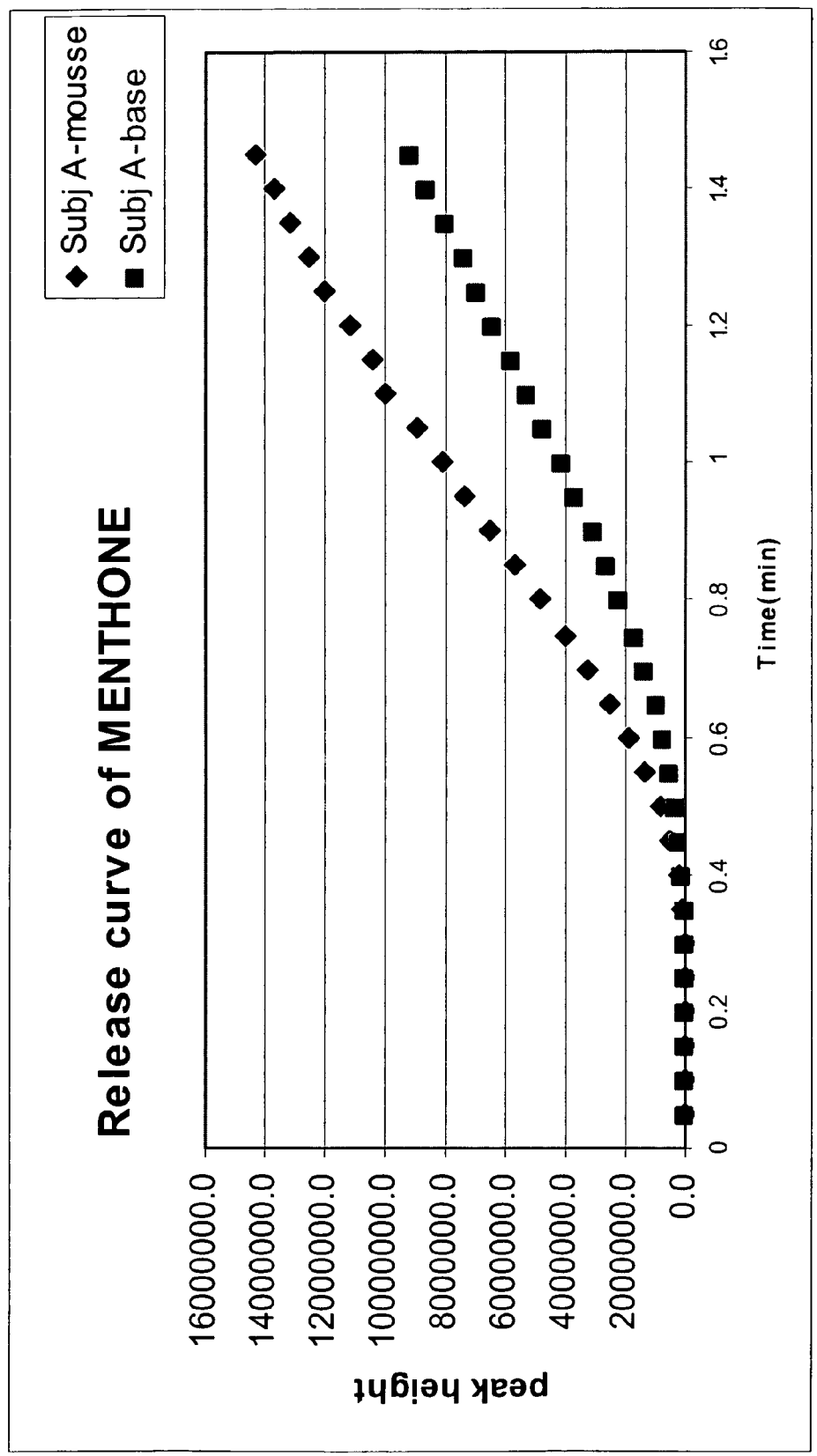
FIG. 1 is a flavor release profile showing release of menthone flavorant from a mousse of the invention and a comparative control composition over time in the oral cavity of a user as measured by atmospheric pressure chemical ionization mass spectrometry.

The present invention includes an oral care mousse that provides a unique visual and flavor experience during use and also serve to deliver therapeutic benefits to the user. The oral care mousse of the invention is post-foaming, i.e., a dentifrice composition that is dispensed from a container in a substantially gelatinous form and begins to foam after a brief time delay, for example between 0.1 and 1 seconds. For example, certain composition of the invention, when dispensed and exposed to atmospheric pressure, may exhibit a minimal or insignificant amount of foaming immediately upon release but shall develop foam after an initial period of about 0.1 to about 1 seconds or more. The time delay of foaming leads results in a perceptible delay in the onset of foam after dispensing when compared to other aerosol type containers and dispensers that develop foam upon exit from the dispensing valve. Advantageously, this delay reduces or eliminates foaming at the point from which it is dispensed, for example, the dispensing valve.

The oral care mousse of the invention contains a dentifrice composition. The dentifrice compositions contain at least one or more surfactants and one or more humectants. Surfactants to be used in the invention include any known or to be developed in the art or mixtures of the same, including anionic, cationic, nonionic, and amphoteric surfactants. Suitable anionic surfactants include water-soluble salts of $C_{8-20}$ alkyl sulfates, sulfonated monoglycerides of $C_{8-20}$ fatty acids, sarcosinates, and taurates. More specific illustrative examples include sodium lauryl sulfate, sodium coconut monoglyceride sulfonate, sodium lauryl sarcosinate, sodium lauryl isoethionate, sodium laureth carboxylate, sodium dodecyl benzenesulfonate, poloxamers, polyoxyethylene sorbitan esters, fatty alcohol ethoxylates, alkylphenol ethoxylates, tertiary amine oxides, tertiary phosphine oxides, dialkyl sulfoxides, derivatives of $C_{8-20}$ aliphatic secondary and tertiary amines having an anionic group such as carboxylate, sulfate, sulfonate, phosphate or phosphonate. A suitable example is cocamidopropyl betaine.

The surfactant(s) may be present in the dentifrice formulation in any amount; however, it may be preferred that one or more surfactants is present in an amount of about 0.01% to about 10%, about 0.05% to about 5% or about 0.1% to about 2% by weight of the dentifrice composition. If desired, the dentifrice composition may include a dual surfactant system of an anionic and an amphoteric surfactant, such as sodium lauryl sulfate powder and cocamidopropyl betaine. Under such circumstances, the dual surfactant system may be about 0.5 to about 2 wt % sodium lauryl sulfate and about 0.5 to about 2.5 wt % cocamidopropyl betaine (a 30% solution), or, more preferably, about 1 to about 1.65 wt % sodium lauryl sulfate and about 1.25 to about 2.5 wt % cocamidopropyl betaine (a 30% solution).

The dentifrice composition of the invention also contains at least a humectant. Any humectant known or to be developed in the art may be included. Specific humectants useful in the dentifrice composition of the invention include polyhydric alcohols such as glycerin, sorbitol, xylitol or low molecular weight PEGs. One or more humectants may be present in an amount up to about 80%, more preferably about 10% to about 70% or about 5% to about 60% by weight of the total dentifrice composition.

The dentifrice compositions may include a flavorant or a mixture of flavorants, including natural or synthetic flavorants, such as flavoring oils, flavoring aldehydes, esters, alcohols, similar materials, and combinations thereof. Volatile flavorants may be preferred. Flavorants may include vanillin, spearmint oil, cinnamon oil, oil of wintergreen (methylsalicylate), peppermint oil, clove oil, anise oil, eucalyptus oil, citrus oils, fruit oils and essences. Particularly preferred may be flavorants such as limonene, menthone, carvone, menthol, anethole, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA) and cineole.

The dentifrice compositions of the invention may contain a binder agent; any conventional binder agent(s) may be utilized. Suitable agents include marine colloids, carboxyvinyl polymers, carrageenans, starches, cellulosic polymers such as hydroxyethylcellulose, carboxymethylcellulose (carmellose), hydroxypropyl methyl cellulose and salts thereof (e.g., carmellose sodium), natural gums such as karaya, xanthan, gum arabic and tragacanth, chitosan, colloidal magnesium aluminum silicate, and colloidal silica.

It may be desirable to include within the dentifrice composition one or more therapeutic agents that prevent, treat and/or reduce the symptoms related to various oral or systemic diseases or conditions. Useful therapeutic agents include all those known or developed in the art including steroids, NSAIDs, a fluoride ion source, polycarboxylate polymers, polyvinyl methyl ether/maleic anhydride (PVME/MA) copolymers, an arginine ester, a zinc ion source, a stannous ion source, delmopinol, tartar control agents, an antibacterial agent, triclosan and salts thereof, chlorhexidine, alexidine, hexetidine, sanguinarine, benzalkonium chloride, salicylanilide, domiphen bromide, cetylpyridinium chloride (CPC), tetradecylpyridinium chloride (TPC), N-tetradecyl-4-ethylpyridinium chloride (TDEPC), octenidine, octapinol, nisin, a zinc ion source, a copper ion source, an essential oil, a furanone, anti-inflammatory agents, antiplaque agents, antioxidants, and a bacteriocins, and salts thereof, honokiol, vitamins, anti-attachment agents, proteinaceous agents, peptides. A further illustrative list of useful antibacterial agents is provided in U.S. Pat. No. 5,776,435, the contents of which are incorporated herein by reference.

Abrasives may be added to the dentifrice formulation if desired. Any suitable oral care abrasive or polishing agent may be used. Preferred may be silica abrasives such as precipitated silicas, sodium metaphosphate, potassium metaphosphate, tricalcium phosphate, dihydrated dicalcium phosphate, aluminum silicate, calcined alumina, bentonite or other siliceous materials, particulate thermosetting resins, such as melamine, phenolic, and urea-formaldehydes, and cross-linked polyepoxides and polyesters.

As desired, any other additives may be included in the dentifrice composition for reasons of e.g., manufacturing, stability, aesthetics, therapeutic effect, consumer appeal, etc. Exemplary additives include all other conventional dentifrice additives, viscosity modifiers, diluents, foam modulators, saliva stimulating agents, desensitizing agents, whitening agents, enzymes, pH modifying agents, mouth-feel agents, sweeteners, colorants, opacifiers, and breath freshening agents.

As described above, the dentifrice composition of the invention has a viscosity of less than about 30,000 centipoise as determined by a Brookfield viscometer, Model RVTDV-II, spindle E at 5 rpm prior to the addition of the propellant. Alternatively, the viscosity may be about 18,000 to about 23,000 centipoise or about 5,000 to about 15,000 centipoise.

The post-foaming oral care mousse also contains a propellant or mixture of propellants. The selected propellant(s) may be any in the art, and will vary depending on the various factors such as rate of foam expansion desired, environmental regulations, and/or consumer safety concerns. It is preferred that the propellant or mixture of propellants contains a mixture of at least one propellants that has a boiling point of less than about −15° C., alternatively, less than about −10° C. In one embodiment, the propellant is a mixture of two propellants; one which facilitates the egress of the dentifrice composition the container and a second which serves to expand or "post foam" the dentifrice into a mousse.

The propellant may include other agents, as desired, such as blowing agents air, nitrous oxide, and carbon dioxide and, more typically, a volatile hydrocarbon or mixture of volatile hydrocarbons (typically with 3 to 6 carbon atoms) having a vapor pressure of 15 to 80 psig, preferably 30 to 70 psig, at about 20° C.

The preferred propellant has the industry designation A-46 and is a mixture of isobutane and propane with a vapor pressure of 46 psig at about 20° C. The propellant may contain, for example, about 75 to about 85 wt % isobutane and between about 15% to about 25 wt % propane. Once the dentifrice composition and the propellant(s) are mixed together, the resultant emulsion may include about 1 to about 6 wt % of the compressed liquid propellant, more preferably from about 2 to about 3 wt % of the propellant.

Once dispensed, the oral care mousse of the invention is initially in a gel or semi-liquid form. Subsequently, but in less than about five seconds after dispensing, the initial dispensed quantity expands by at least 100% of the initial volume, preferably by about 200% of the initial volume. Preferably, this 100% volume increase and/or 200% volume increase occurs in less than about five seconds or less than about three seconds.

It may be preferred that the post-foaming dental mousse is fully or substantially fully formed and expanded prior to the user inserting the mousse into the oral cavity. In this manner, any delayed gas release is minimized and the user does not experience any undesired flavor which may be encountered from the propellant volatilizing while inside the oral cavity.

Suitable pressure differential dispensers for use with the present invention include those comprising a collapsible product-containing bag being disposed within a rigid container which contains a propellant fluid. As in known in the art with the use of such dispensing containers, operation of a manually actuated dispensing valve permits the release of the gel dentifrice product only, the propellant fluid being separated from the product by the fluid impermeable bag. The fluid impermeable bag systems commonly include bags made of chemically inert polymers and those described in U.S. Pat. Nos. 6,622,943; and 6,789,702, the contents of each of which are incorporated herein by reference.

Various other embodiments may use another type of dispenser commonly known as the barrier piston container described in, e.g., U.S. Pat. No. 4,171,757, the contents of which are incorporated herein by reference. Such a container includes a valve, a product-containing compartment and an essentially fluid-tight barrier piston which separates the propellant fluid from the contained product.

Filling may be effected by conventional techniques. For example, when a mechanically operated dispenser is used, a predetermined amount of the compressed liquid propellant is blended with a predetermined amount of dentifrice, or mousse, and is mixed together as an emulsion. The mixture or emulsion is extruded through a nozzle to fill the dispenser which is open at the bottom and which contains a central rod. A piston having a diameter corresponding to the inner diameter of the dispenser and a central hole to permit insertion of the central rod therein is slid into place. The dispenser is then sealed with a bottom disc.

It should be understood that numerous manually operated dispensers, pumping devices and propelling structures are commercially available, with or without internal bags, and are contemplated for use with the present invention.

The invention also includes oral cares mousses, as described in the various embodiments above, which provided a specific flavor release as measured by atmospheric pressure chemical ionization mass spectrometry, such as the methods described in e.g., Taylor, A. J. et al. (2000) Food Chem. 71: 327-338; Taylor et al. Front. Flv. Sci. 255-260 (hereinafter the "Taylor Technique"), the contents of which are incorporated herein by reference. The method uses an atmospheric pressure inlet system interfaced to a mass spectrometer. Ions that are representative of the analytes of interest are monitored.

For example, the invention includes a post foaming mousse containing a flavorant and otherwise as described above in the various embodiments above and which upon application of the mousse to a user's oral cavity exhibits a flavor release peak after 60 seconds that is greater then the flavor release peak height of a control composition ($P_p$) containing the same flavorant(s). Alternatively, the oral care mousse provides a flavor release peak upon application to a user's mouth after 60 seconds such that the difference between $P_m$ and $P_p$ is about 25% to about 40% or the difference between $P_m$ and $P_p$ is greater than about 30%.

Alternatively, the post foaming oral care mousse is one in which, and wherein average rate of flavor release is 4000 units/sec to 20,000 units/sec in the initial 60 seconds after application to the oral cavity as measured by the Taylor Technique.

Example 1

Oral Care Mousse Preparation

An oral care mousse was prepared. First, the dentifrice composition of the mousse was prepared by combining the ingredients as shown under each column in Table 1, below. Subsequently, a propellant mixture was added to it in an amount of 3% by weight of a mixture of 75% isobutene and 25% propane to form an emulsion. Propellant sold under the name DRIVOSOL® 35A by Technical Propellants, Inc., of Morris Ill., United States was used.

The mousse was loaded into the conventional dual propellant type dispensers as previously described to prepare the dispensing system of the invention.

TABLE 1

|  | Wt % |
|---|---|
| Glycerin | 8.0 |
| Demineralized water | 9.0 |
| Polyethylene glycol 600 | 1.4 |

TABLE 1-continued

|  | Wt % |
|---|---|
| Carrageenan concentrate | 0.5 |
| Sodium saccharin | 0.350 |
| Sorbitol (70% solution in water) | 62.277 |
| Color solution | 0.08 |
| Tetrasodium pyrophosphate | 0.5 |
| Sodium fluoride | 0.243 |
| Silica | 13.3 |
| Sodium lauryl sulfate | 1.0 |
| Cocamidopropyl betaine (30% solution in water) | 2.0 |
| Flavor | 1.35 |
| TOTAL | 100.000 |

Example 2

Measurement of Flavor Release Profile of Mousse

An oral care mousse of the invention ("A") and a comparison control non-mousse composition ("B") were prepared. To prepare A, a dentifrice composition was prepared by combining the ingredients as shown in Table 1, above. The propellant mixture specified in Example 1 above was added. The emulsion was loaded into a bag-on-valve dispenser.

To prepare B, a composition was formed by combining the ingredients as shown in Table 1. No propellant was added to the formulation.

The flavor used in both the mousses A and the control composition B contains four flavorants (among others): limonene, menthone, carvone, and menthol.

Using the Taylor technique, the flavor profiles of each sample were quantified. The cavity samples were drawn from the oral cavity of an individual by collecting air from the oral cavity during brushing with 1 gram of sample. The air was collected directly to the analytical device. Such collection process added a minimal time delay from the initial collection time to the time the instrument recorded the data. This can be seen in FIGS. 1-4. Thus, data obtained at any time point reflects the conditions in the oral cavity at a time point approximately 30 seconds earlier. Direct measurement of the headspace in the oral cavity was carried out to analytically determine the initial flavor release over the brushing time for each of the samples.

The release curves generated for each flavorant of the mousse/control composition comparison are shown in FIGS. 1-4. Table 4 below summarizes the peaks of the flavor profiles after the passage of time. $P_m$ represents a peak for the mousse formulation and $P_p$ represents a peak for the control composition.

TABLE 4

Figure 2:
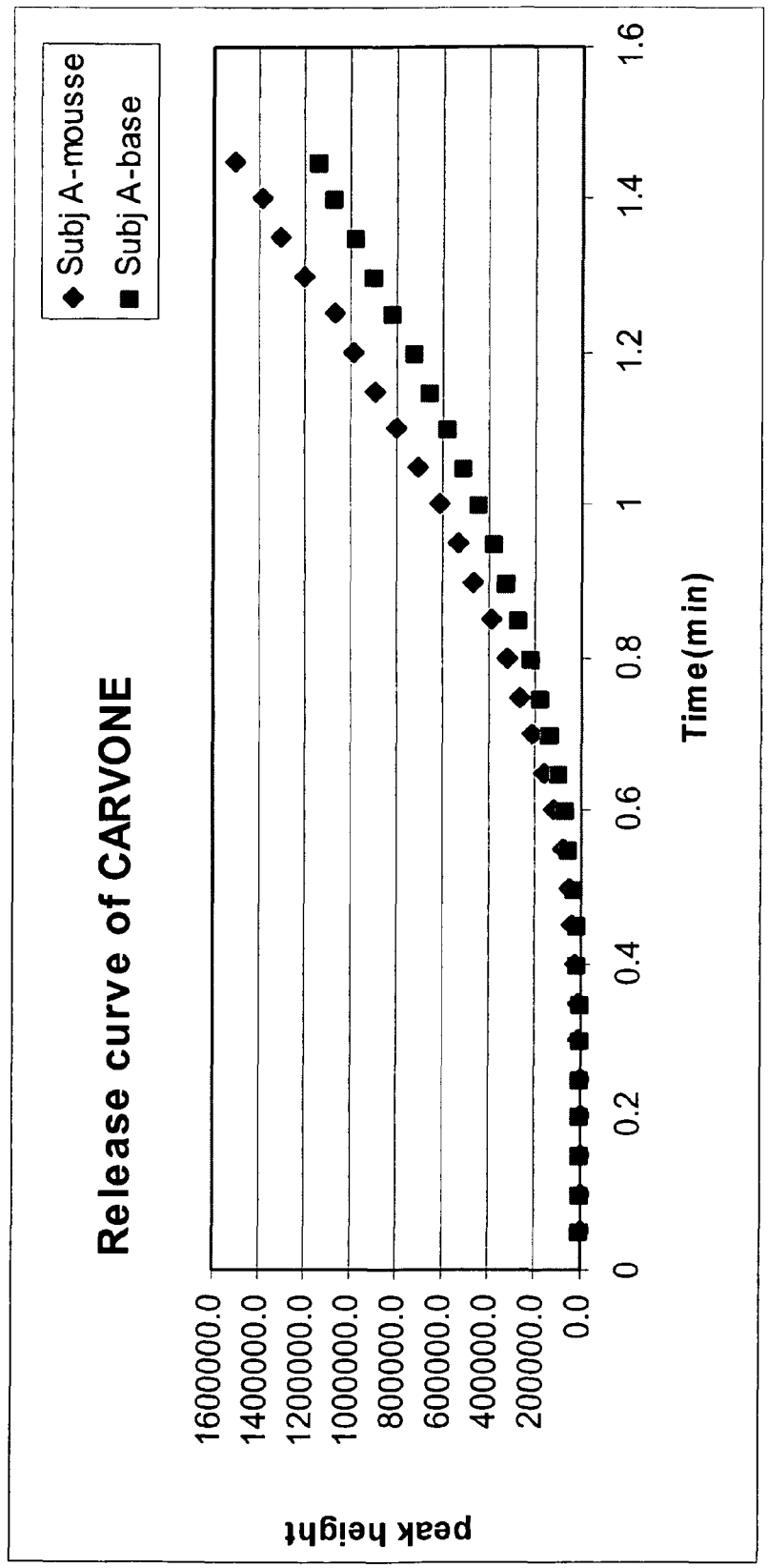
FIG. 2 is a flavor release profile showing release of carvone flavorant from a mousse of the invention and a comparative control composition over time in the oral cavity of a user as measured by atmospheric pressure chemical ionization mass spectrometry.
Figure 3:
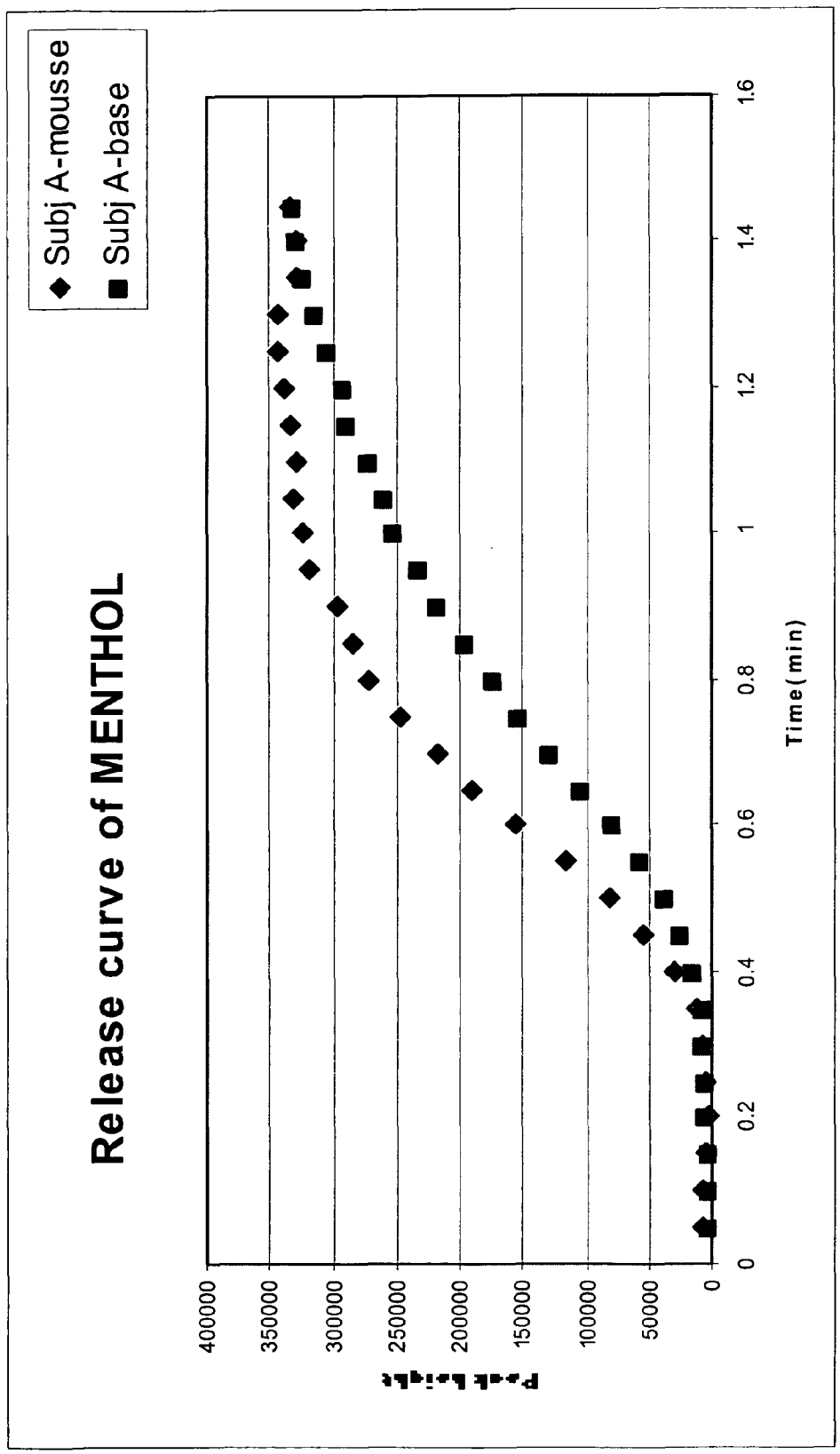
FIG. 3 is a flavor release profile showing release of menthol flavorant from a mousse of the invention and a comparative control composition over time in the oral cavity of a user as measured by atmospheric pressure chemical ionization mass spectrometry.
Figure 4:
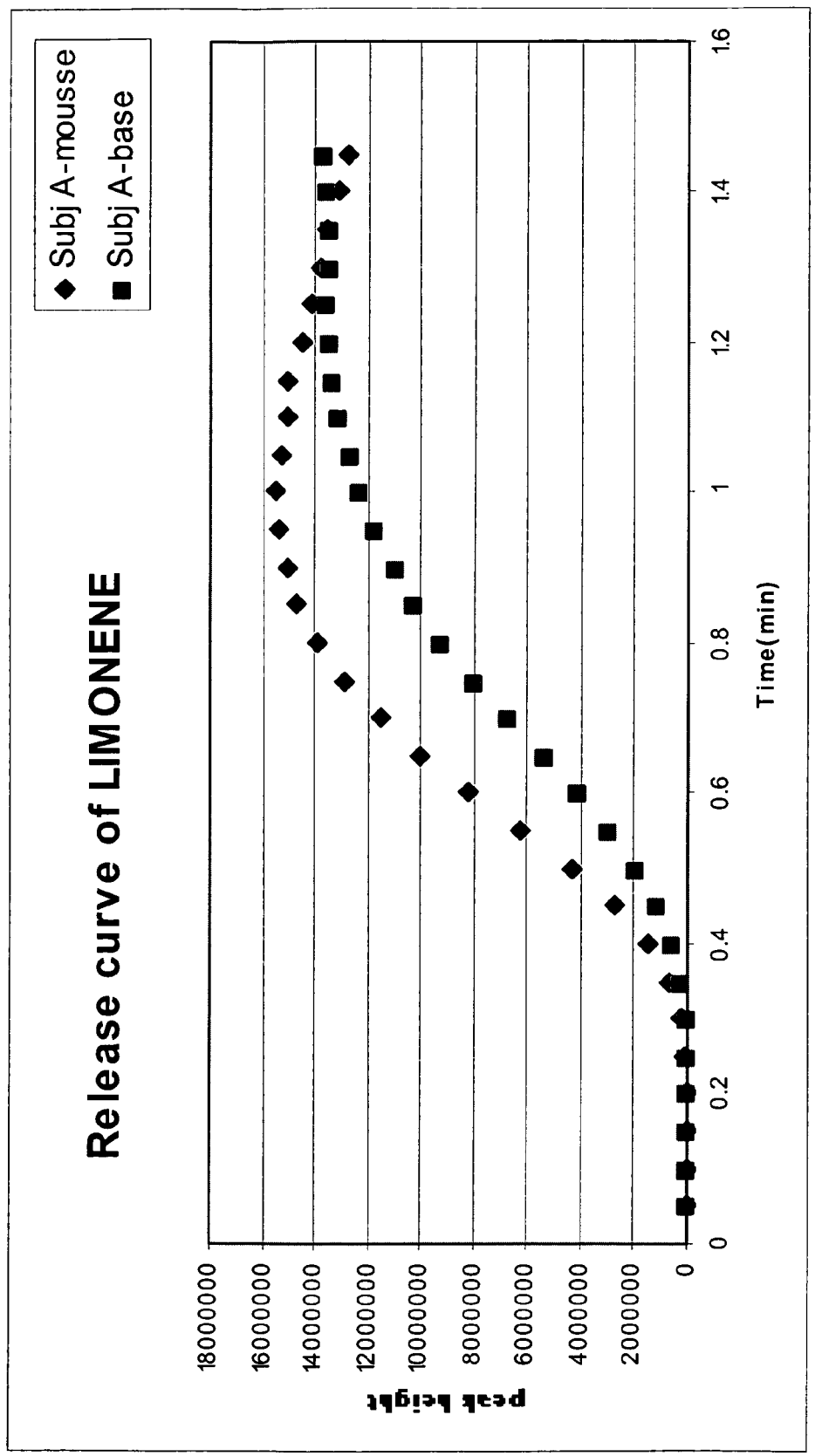
FIG. 4 is a flavor release profile showing release of limonene flavorant from a mousse of the invention and a comparative control composition over time in the oral cavity of a user as measured by atmospheric pressure chemical ionization mass spectrometry.

|  | $P_m$ | $P_p$ |
|---|---|---|
| FIG. 1 Release Curve for menthone | Approximately $140 \times 10^5$ at 60 seconds | Approximately $80 \times 10^5$ at 60 seconds |
| FIG. 2 Release Curve for carvone | Approximately less than $160 \times 10^5$ at 60 seconds | Approximately $120 \times 10^5$ at 60 seconds |
| FIG. 3 Release Curve for menthol | Approximately $350 \times 10^3$ at 42 seconds | Approximately $300 \times 10^3$ at 42 seconds |
| FIG. 4 Release Curve for limonene | Approximately $160 \times 10^5$ at 30 seconds | Approximately $120 \times 10^5$ at 30 seconds |

As can be seen from the Figures and the summary chart above, in each case the $P_m$ is higher than the $P_p$ at an earlier point in time.

We claim:

1. A post foaming oral care mousse comprising: (a) a dentifrice composition that comprises a surfactant and a humectant; and (b) a compressed liquid propellant that has a boiling point of less than −10° C., wherein the composition of (a) has a viscosity of less than 30,000 centipoise, as determined by a Brookfield viscometer, Model RVTDV-II, spindle E at 5 rpm prior to the addition of propellant, and the mousse is dispensed as a gel that expands at least 100 vol % in less than 5 seconds.

2. The mousse according to claim 1, wherein the composition of (a) has a viscosity of about 18,000 to about 23,000 centipoise.

3. The mousse according to claim 1, wherein the mousse expands at least 100 vol % in less than 3 seconds.

4. The mousse according to claim 1, wherein the mousse expands at least 200 vol % in less than 5 seconds.

5. The mousse according to claim 4, wherein the mousse expands at least 200 vol % in less than 3 seconds.

6. The mousse according to claim 1, wherein the propellant comprises a mixture of propane and isobutane.

7. The mousse according to claim 1, wherein the propellant comprises about 75 to about 85 wt % isobutane and about 15 to about 25 wt % propane.

8. The mousse according to claim 1, wherein the propellant is present in the mousse in an amount of about 1 to about 6 wt %.

9. The mousse according to claim 1, wherein the surfactant is selected from sodium lauryl sulfate, a betaine surfactant, and cocamidopropyl betaine.

10. The mousse according to claim 1, wherein the surfactant comprises about 0.5 to about 2 wt % sodium lauryl sulfate and about 0.5 to about 2.5 wt % cocamidopropyl betaine.

11. The mousse according to claim 1, wherein the composition of (a) further comprises a binder agent.

12. The mousse according to claim 11, wherein the binder agent is selected from carrageenan, chitosan, agar, xanthan gum, guar gum, starch, a cellulosic polymer, and a marine colloid.

13. The mousse of claim 1, wherein the composition further comprises an agent selected from a fluoride ion source, an arginine ester, a zinc ion source, a stannous ion source, delmopinol, an antibacterial agent, and triclosan and salts thereof.

14. The mousse of claim 1, wherein the composition further comprises an agent selected from chlorhexidine, alexidine, hexetidine, sanguinarine, benzalkonium chloride, salicylanilide, domiphen bromide, cetylpyridinium chloride (CPC), tetradecylpyridinium chloride (TPC), N-tetradecyl-4-ethylpyridinium chloride (TDEPC), octenidine, octapinol, nisin, a zinc ion source, a copper ion source, an essential oil, a furanone, an enzyme, a peptide, a protein, a bacteriocin and salts thereof and honokiol.

15. The mousse according to claim 1, further comprising an abrasive.

16. A system for dispensing an oral care mousse, comprising a dentifrice and dispenser, wherein the dentifrice comprises (a) a dentifrice composition that comprises a surfactant and a humectant; and (b) a compressed liquid propellant that has a boiling point of less than −10° C., and the composition of (a) has a viscosity of less than 30,000 centipoise, as determined by a Brookfield viscometer, Model RVTDV-II, spindle E at 5 rpm, prior to the addition of the propellant and the mousse is adapted to be dispensed from a container as a gel that expands at least 100 vol % in less than 5 seconds and the dispenser comprises a dual propellant assembly.

17. The system according to claim 16, wherein the dispenser comprises a piston assembly.

18. The system according to claim 16, wherein the dispenser comprises a bag-in-can assembly.

19. A post foaming oral care mousse comprising: (a) a dentifrice composition that comprises a surfactant, a flavorant, and a humectant; (b) a compressed liquid propellant that has a boiling point of less than −10° C., wherein the composition of (a) has a viscosity of less than 30,000 centipoise, as determined by a Brookfield viscometer, Model RVTDV-II, spindle E at 5 rpm, prior to the addition of the propellant and upon application of the mousse to a user's oral cavity, the flavor release peak height of the mousse ($P_m$) at 60 seconds is greater than the flavor release peak height of a control composition ($P_p$) containing the same flavorant.

20. The mousse according to claim 19, wherein the difference between $P_m$ and $P_p$ is about 25% to about 40%.

21. The mousse according to claim 19, wherein the difference between $P_m$ and $P_p$ is greater than about 30%.

22. A post foaming oral care mousse comprising: (a) a dentifrice composition that comprises a surfactant, a flavorant, and a humectant; (b) a compressed liquid propellant that has a boiling point of less than −10° C., wherein the composition of (a) has a viscosity of less than 30,000 centipoise, as determined by a Brookfield viscometer, Model RVTDV-II, spindle E at 5 rpm, prior to the addition of the propellant and upon application of the mousse to a user's oral cavity, and wherein average rate of flavor release is 4000 units/sec to 20,000 units/sec in the initial 60 seconds after application to the oral cavity.

* * * * *